(12) United States Patent
McDonald (10) Patent No.: US 7,175,432 B2
(45) Date of Patent: Feb. 13, 2007

(54) DENTAL CONTACT MATRIX LIMITED

(75) Inventor: Simon Paul McDonald, Katikati (NZ)

(73) Assignee: Tri-Dent Innovations Limited, Bay of Plenty (NZ)

( * ) Notice: Subject to any disclaimer, the term of this patent is extended or adjusted under 35 U.S.C. 154(b) by 170 days.

(21) Appl. No.: 10/495,120

(22) PCT Filed: Nov. 19, 2002

(86) PCT No.: PCT/IB02/04824

§ 371 (c)(1),
(2), (4) Date: Aug. 19, 2004

(87) PCT Pub. No.: WO03/043521

PCT Pub. Date: May 30, 2003

(65) Prior Publication Data

US 2004/0265779 A1   Dec. 30, 2004

(30) Foreign Application Priority Data

Nov. 19, 2001 (NZ) .................................. 515528
Dec. 6, 2001 (NZ) .................................. 515947
Feb. 7, 2002 (NZ) .................................. 517032

(51) Int. Cl.
*A61C 3/00* (2006.01)
*A61C 5/12* (2006.01)
*A61C 5/04* (2006.01)
*A61C 7/00* (2006.01)

(52) U.S. Cl. ...................... 433/153; 433/155; 433/139; 433/149

(58) Field of Classification Search ................ 433/155, 433/153, 149, 148, 162, 156
See application file for complete search history.

(56) References Cited

U.S. PATENT DOCUMENTS

| 164,870 A | 6/1875 | Palmer |
| 368,988 A | 8/1887 | Williams |
| 388,620 A | 8/1888 | Booth |
| 2,090,904 A | 8/1937 | Singer ........................ 32/63 |
| 2,150,005 A | 3/1939 | McNinch ..................... 32/64 |
| 2,629,930 A | 3/1953 | Lane ........................... 32/63 |
| 4,259,070 A | 3/1981 | Soelberg et al. ............ 433/149 |

(Continued)

FOREIGN PATENT DOCUMENTS

CH   387223   1/1965

(Continued)

*Primary Examiner*—Cary E. O'Connor
(74) *Attorney, Agent, or Firm*—Jacobson Holman PLLC (57) ABSTRACT

A dental contact matrix system is described for the placement of dental fillings. The dental contact matrix system includes a matrix, a retainer for placing and retaining the 5 matrix and an elastic wedge. The retainer includes two lugs or tines that fit between two teeth on the buccal and lingual sides of the teeth. The lugs are connected by spring member that presses the lugs against the lingual and buccal sides of the teeth. There is an adaptation to hold the elastic wedge in a stretched condition between the lugs.

27 Claims, 12 Drawing Sheets

U.S. PATENT DOCUMENTS

| | | | | |
|---|---|---|---|---|
| 4,718,852 A | * | 1/1988 | Galler | 433/148 |
| 4,787,849 A | * | 11/1988 | Jacoby et al. | 433/139 |
| 5,607,302 A | * | 3/1997 | Garrison et al. | 433/39 |
| 6,059,568 A | * | 5/2000 | Munro et al. | 433/23 |
| 6,206,697 B1 | * | 3/2001 | Hugo | 433/155 |
| 6,336,810 B1 | * | 1/2002 | Bertoletti | 433/39 |
| 6,435,874 B1 | | 8/2002 | Hughes | 433/149 |
| 2002/0155410 A1 | * | 10/2002 | Bills | 433/153 |

FOREIGN PATENT DOCUMENTS

| | | |
|---|---|---|
| CH | 669514 | 3/1989 |
| EP | 0097266 | 1/1984 |
| EP | 0668060 | 5/2001 |
| FR | 2820024 | 8/2002 |
| GB | 435004 | 9/1935 |
| WO | WO96/18353 | 6/1996 |
| WO | WO96/39984 | 12/1996 |

* cited by examiner

DENTAL CONTACT MATRIX LIMITED

This is a nationalization of PCT/IB02/04824 filed Nov. 19, 2002 and published in English.

1. Field of the Invention

The present invention relates to an apparatus for the placement of dental fillings and in particular light curable dental fillings.

2. Summary of the Prior Art

The dental profession has moved over the last two or so decades from the use of mercury based fillings to the use of composite resins that are used to provide natural looking fillings. Composite resin is cured by the application of concentrated light. To enable the dental professional to place composite resin fillings matrixes are used. A matrix which is a device which wraps around the tooth and acts as a mould to contain the composite resins before they are cured. Matrices are generally formed of plastic or stainless steel and are either circumferential or sectional. Sectional matrices fit only in one proximal area of the tooth while circumferential matrix bands fit around the entire circumference of the tooth. In the prior art matrixes are secured in place by the use of wedges and/or clamps. Wedges are generally made of wood or plastic and are placed between the matrix and an adjacent tooth. Wedges are used to hold the matrix against the tooth being filled and to temporarily separate the tooth being filled and the adjacent tooth.

In the prior art wedges and other matrix support means are used to hold the matrices in place. The use of separate components makes it cumbersome to place matrices and requires the dental professional to undertake multiple steps in order to secure the matrix.

SUMMARY OF THE INVENTION

It is therefore an object of the present invention to provide a system for securing dental matrices which is an improvement on the prior art systems and devices or which will at least provide the industry with a useful choice.

In a first aspect the present invention consists in a retainer for placing and retaining a matrix in a dental contact matrix system, and for use in conjunction with an elastic "wedge", said retainer comprising:

a first lug, to fit on one side of a proximal contact between two teeth, a second lug to fit on the other side of said proximal contact, a spring member connecting between said first lug and said second lug, said spring member holding said lugs such that they must be separated to fit over said proximal contact, wherein the spring member applies a restorative force pressing said lugs against opposed sides of said proximal contact, and means for receiving and holding an elastic wedge in a stretched condition to span between said first lug and said second lug.

Elastic "wedge" refers to any resilient elastic member for introduction into the inter-proximal space between two teeth in a stretched condition, subsequent release of the stretched condition leading to a lateral expansion of the wedge within the inter-proximal space.

In a second aspect the present invention consists in a dental contact matrix system including a retainer for placing and retaining a matrix in a dental contact matrix system, an elastic "wedge" and a matrix, said retainer comprising:

a first lug, to fit on one side of a proximal contact between two teeth and a second lug to fit on the other side of said proximal contact, a spring member connecting between said first lug and said second lug, said spring member holding said lugs such that they must be separated to fit over said proximal contact, wherein the spring member applies a restorative force pressing said lugs against opposed sides of said proximal contact, said elastic wedge being held in a stretched condition spanning between said first lug and said second lug.

In a third aspect the present invention consists in a retainer for placing and retaining a matrix in a dental contact matrix system, and for use in conjunction with an elastic "wedge", said retainer comprising:

a first lug, to fit on one side of a proximal contact between two teeth, a second lug to fit on the other side of said-proximal contact, a first matrix support member positioned to retain a matrix against said first lug, a second matrix support member positioned to retain a matrix against said second lug, and a spring member connecting between said first lug and said second lug, said spring member holding said lugs such that they must be separated to fit over said proximal contact, wherein the spring member applies a restorative force pressing said lugs against opposed sides of said proximal contact.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

BRIEF DESCRIPTION OF THE DRAWINGS

One preferred form of the present invention will now be described with reference to the accompanying drawings in which.

DETAILED DESCRIPTION OF THE PRESENT INVENTION

Figure 1:
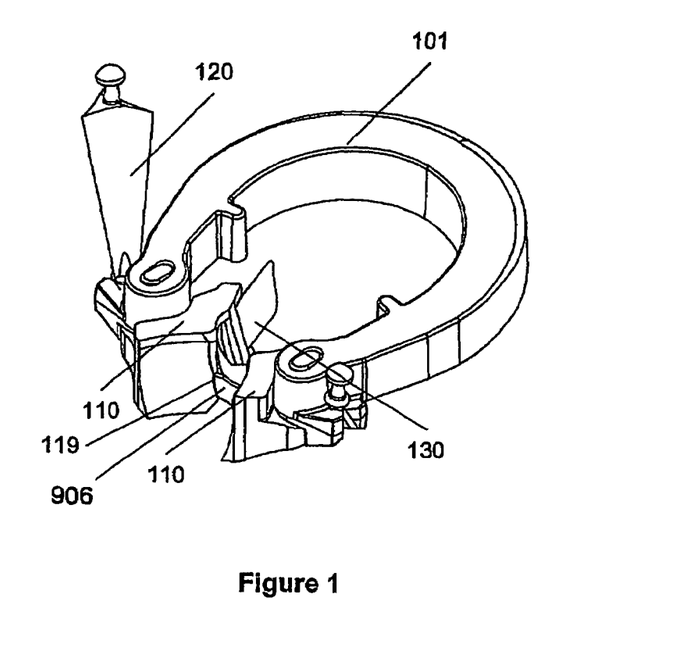
FIG. 1 is a three-dimensional view of the dental matrix system according to the present invention.
Figure 4:
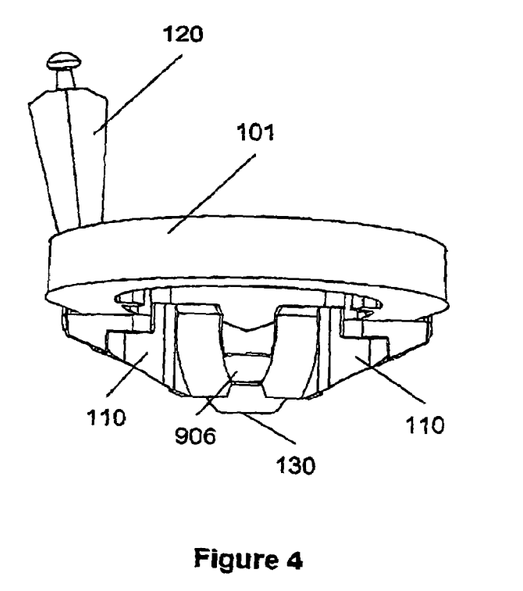
FIG. 4 is an alternative end view of the dental contact matrix system of the present invention.
Figure 5:
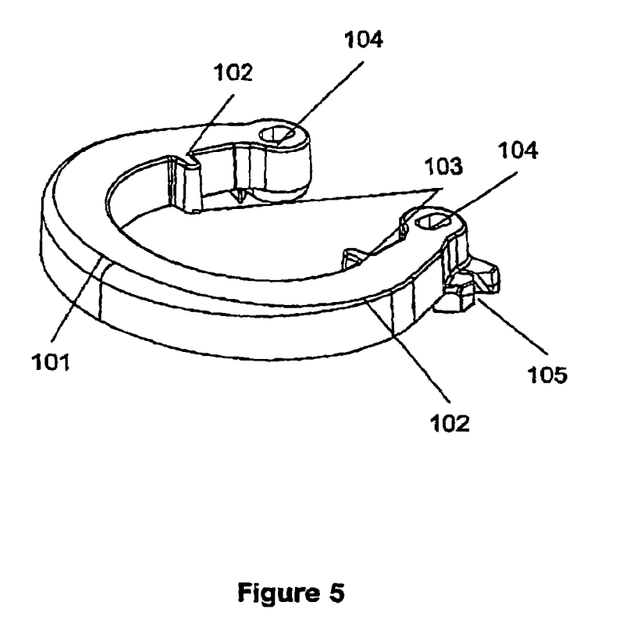
FIG. 5 is a three-dimensional view of the spring of the present invention.
Figure 6:
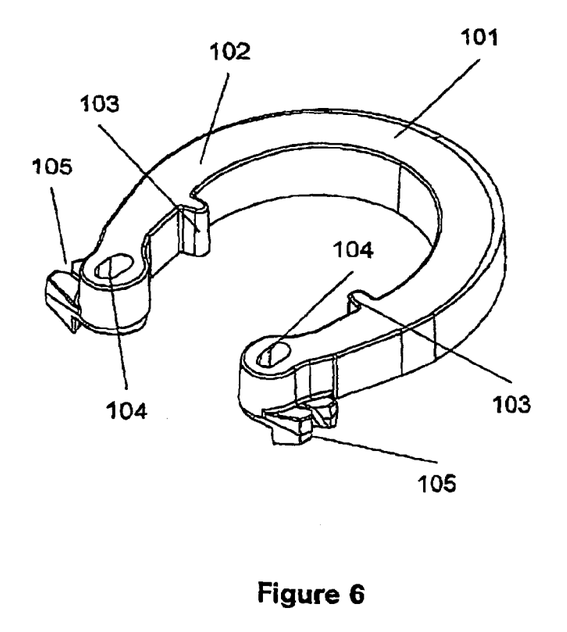
FIG. 6 is an alternative three-dimensional view of the spring of the present invention

Referring to FIGS. 1 and 4 there is shown the dental contact matrix system according to the most preferred embodiment of the present invention. The dental contact matrix system includes a retainer with a spring 101 and two lugs 110 attached to the spring 101. A matrix 130 is held in place by lugs 110 and an elastic wedge 120 is wrapped under the two lugs 110 and the spring 101.

The retainer includes means for receiving and holding the elastic wedge in a stretched condition. The preferred means include a guide on each lug in the form of channels 119. Preferably the means also include a wedge engagement associated with each lug. In the preferred embodiment these are cleats 105.

Figure 7:
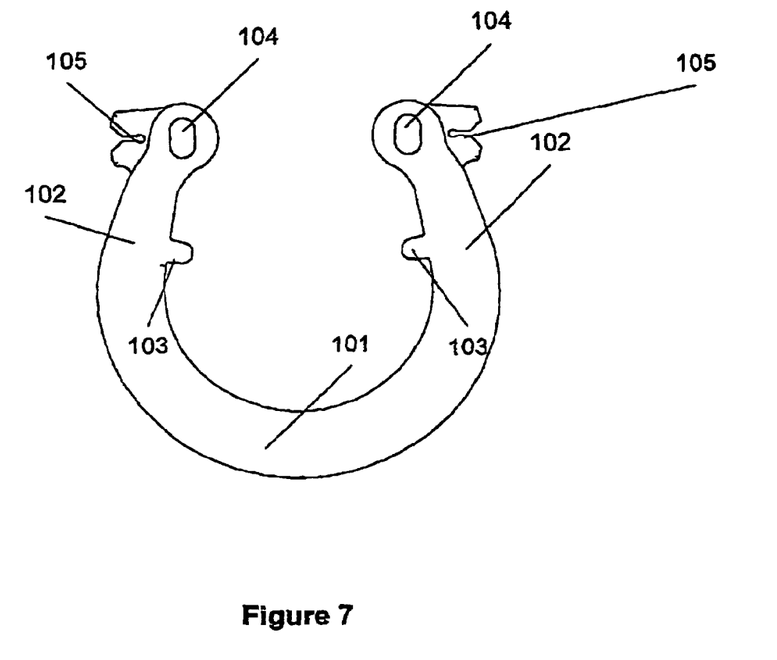
FIG. 7 is a top plan view of the spring of the present invention.
Figure 8:
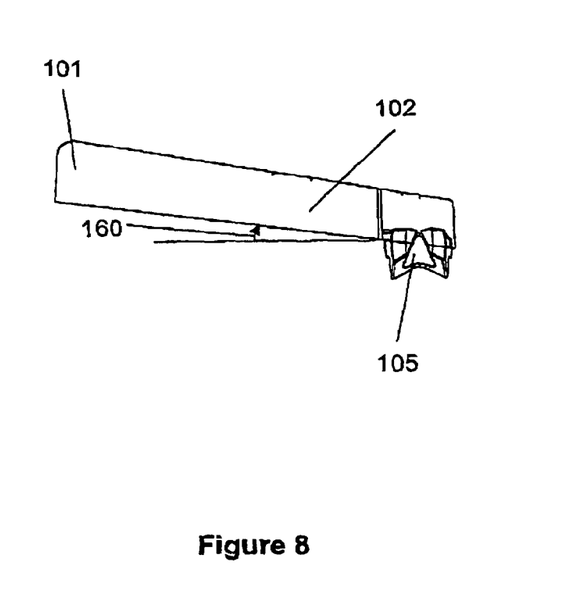
FIG. 8 is a side view of the spring of the present invention.

Referring to FIG. 7 spring 101 is generally semi circular or U-shaped in plane view. Referring to FIGS. 5 to 8 the spring has two arms 102 under tension. The arms 102 require force to push them apart. The dental professional pushes the arms 102 apart using rubber dam forceps or another similar tool. Each arm 102 has a protrusion 103 to stop the rubber dam forceps from slipping while they are used to expand the spring 101. Each arm 102 has an oval shaped hole or socket 104 to enable the lugs 110 to be attached to the spring 101. The use of an oval shape hole 104 prevents the lugs from rotating relative to the arms 102. A channel 105 in each arm allows for the elastic wedge 120 to be attached to the spring 101 and cleated. The channel 105 includes a narrow neck through which narrow sections of the wedge can squeeze. Many alternative forms of connection for the ends of the wedge to the retainer can also be envisaged, including connection to the lugs rather than the spring member. However with lugs that are not integral with the spring member, the present form provides the advantage that the elastic wedge also servers to secure the lugs to the spring member when assembled Spring 101 is formed of material such as plastic or metal.

Figure 9:
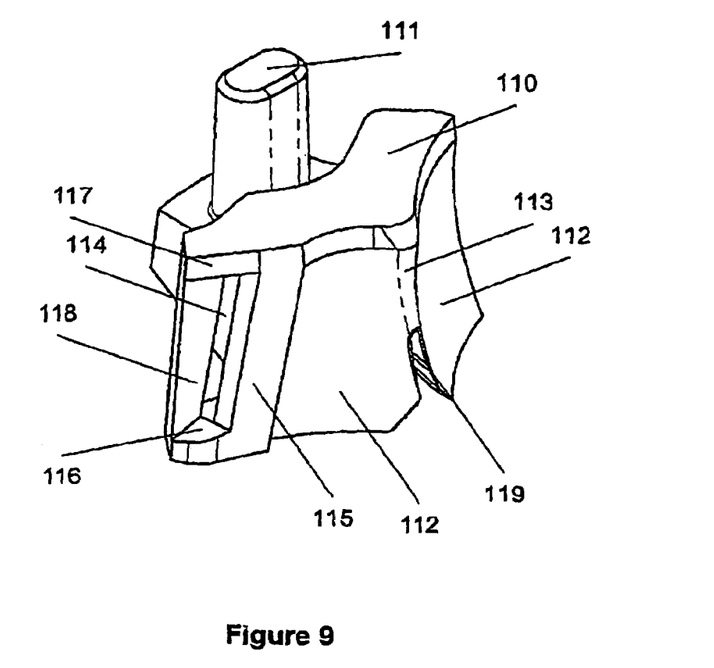
FIG. 9 is a three dimensional view of one of the lugs of the present invention.
Figure 10:
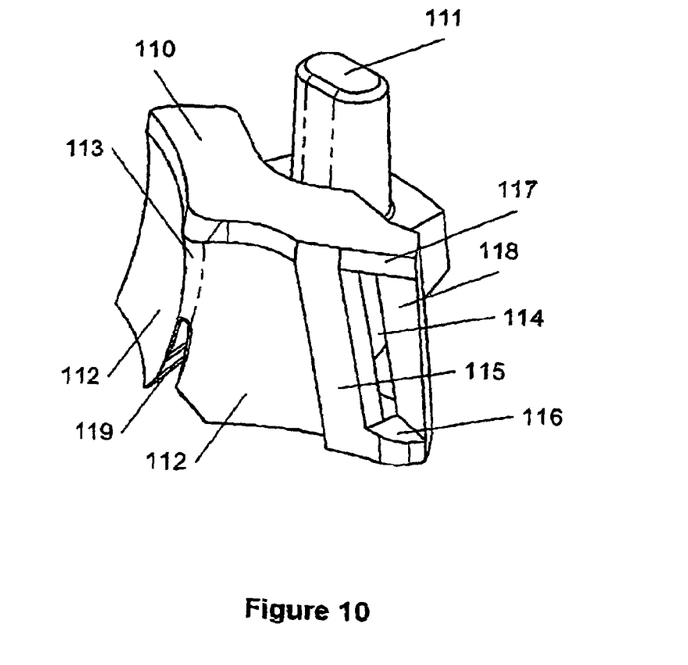
FIG. 10 is a three dimensional view of the other lug of the present invention.
Figure 11:
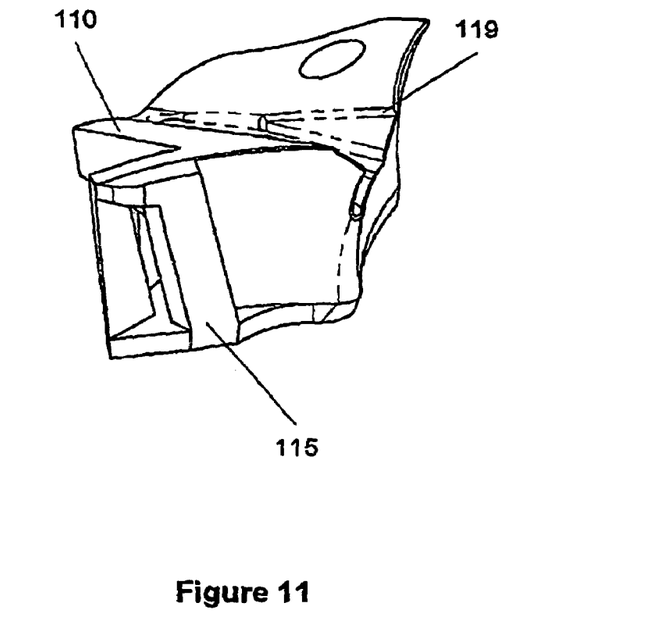
FIG. 11 is a three dimensional view of the lug of the present invention viewing the lug from the bottom.
Figure 12:
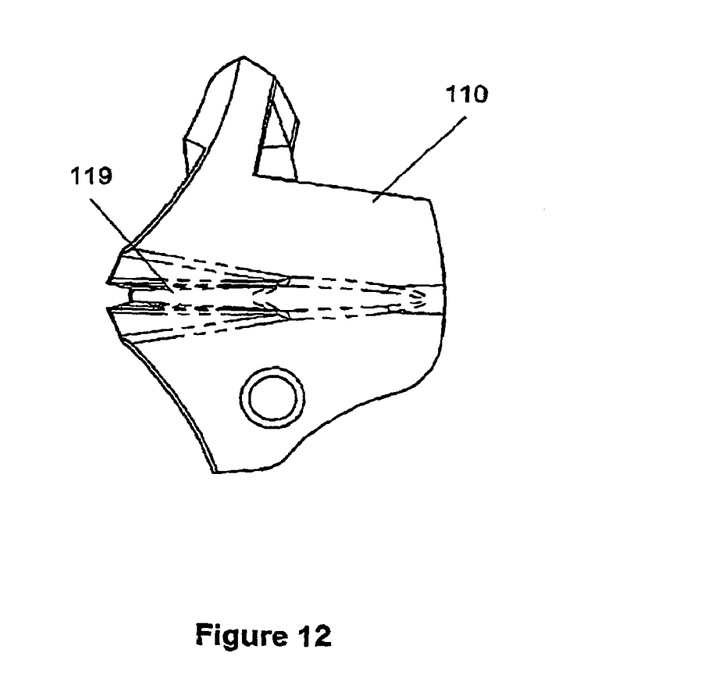
FIG. 12 is a plan view of the bottom of the lug of the present invention.
Figure 13:
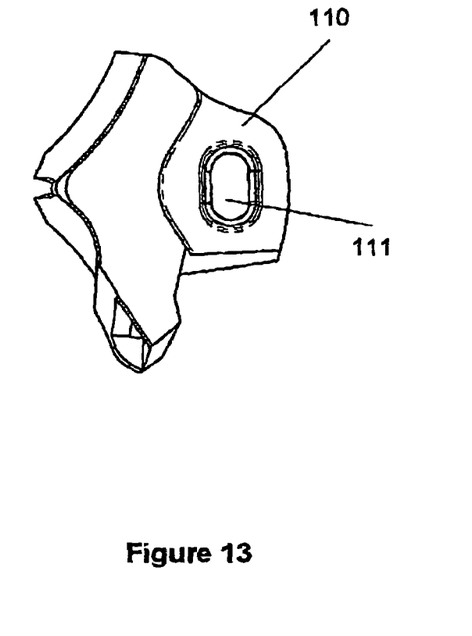
FIG. 13 is a top plan view of the lug of the present invention.
Figure 14:
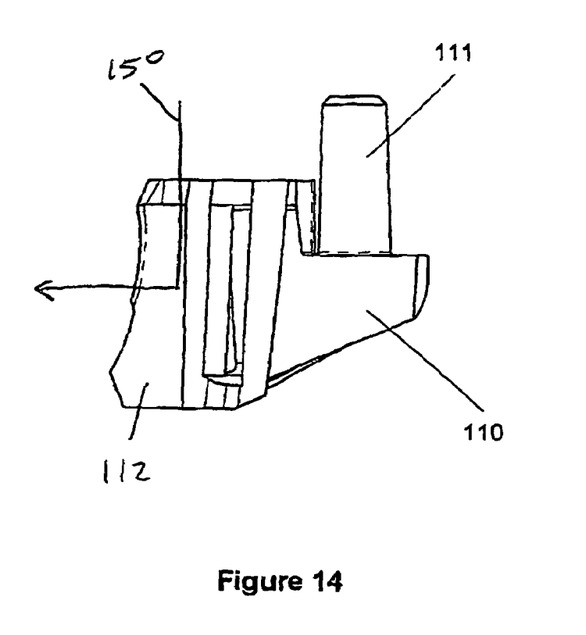
FIG. 14 is a side view of the lug of the present invention.
Figure 15:
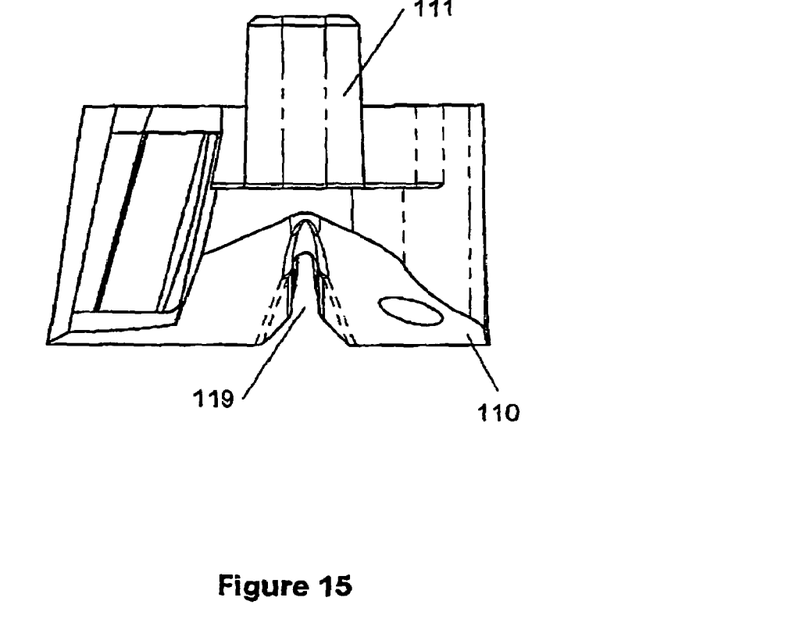
FIG. 15 is a back-view of the lug of the present invention.
Figure 16:
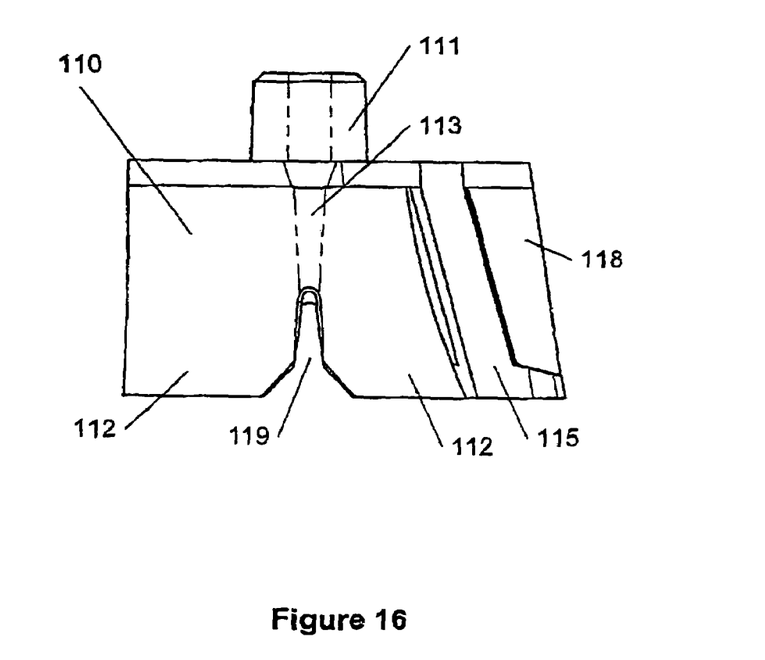
FIG. 16 is a front view of the lug of the present invention.
Figure 17:
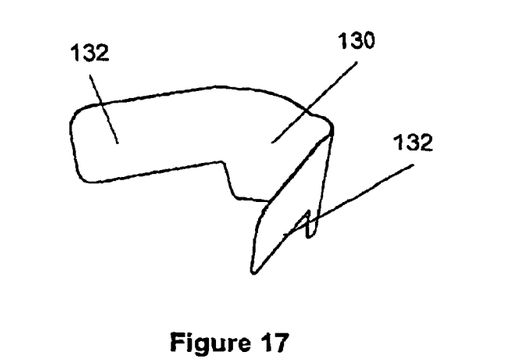
FIG. 17 is a three dimensional view of the matrix of the present invention.
Figure 18:
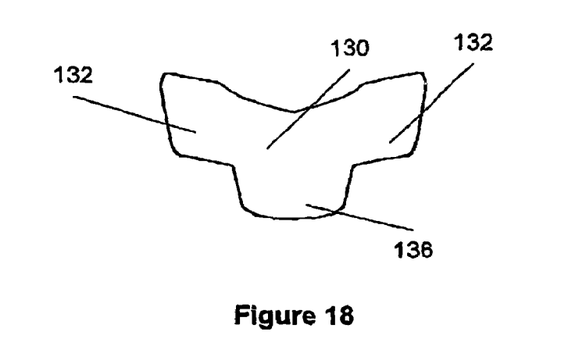
FIG. 18 is a front view of the matrix of the present invention.
Figure 19:
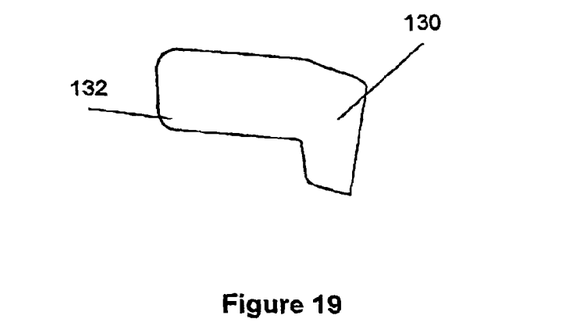
FIG. 19 is a side view of the matrix of the present invention.
Figure 20:
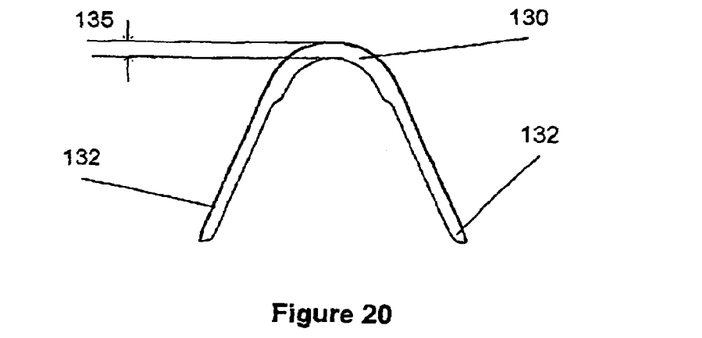
FIG. 20 is a top plan view of the matrix of the present invention.
Figure 21:
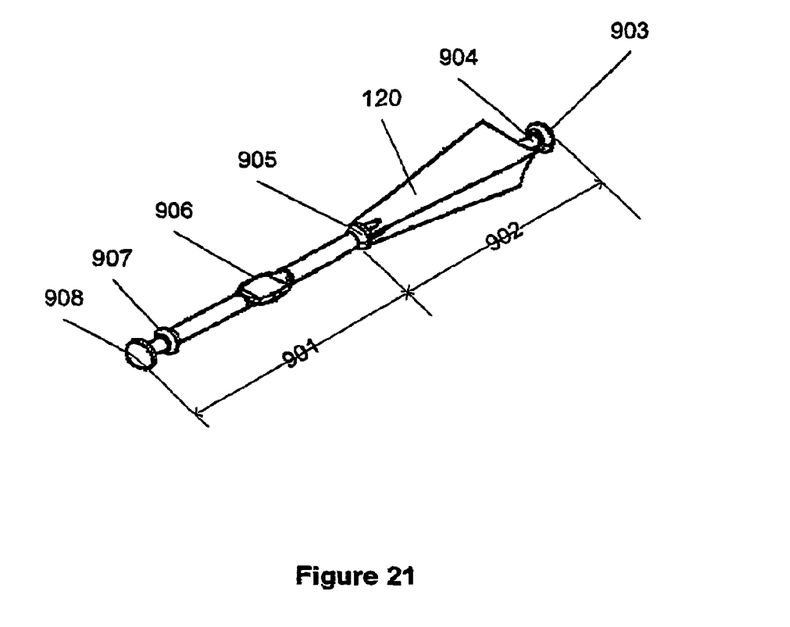
FIG. 21 is a three dimensional view of the wedge of the present invention.

Referring to FIGS. 9 to 16 the lugs 110 are connected to the spring 101 by an oval shaped plug or dowel 111 that fits into the socket 104 in the arms 102 of the spring 101. Each lug 110 is detachable from the spring 101 but in use each lug is attached to a spring arm 102. The lugs are mirror images of each other. FIG. 9 shows one lug 110 and FIG. 10 shows the mirror image lug. In the preferred embodiment each lug 110 is wedge shaped to enable it to fit in proximal contact between two teeth.

Lug faces 112 in use abut the tooth being filled and the neighbouring tooth. The lug faces are in the preferred embodiment concave so as to adapt to the inter-proximal space between teeth. A ridge 113 at the intersection of the faces projects into the inter-proximal space between the two teeth. In use one lug fits on the lingual side and the other lug on the buccal side.

The lugs 110 connect to the spring 101, so that in general the placement of the spring path is substantially perpendicular to the line of ridge 113. However the sockets 104 in the spring are offset at an angle 160 shown in FIG. 8 so that the spring slopes up slightly from perpendicular. This enables the spring in use to be above neighbouring teeth to the tooth being filled. In an alternative embodiment the lugs could be taller so that the spring would clear neighbouring teeth. The path and position of the spring allow unobstructed viewing of the proximal contact.

Each lug 110 has a matrix holder to hold the matrix 130 in place. In the preferred embodiment the holder is a slot 114 used to retain the matrix 130. A support member 115 and a bottom 116 and top ledge 117 create the slot and retain the matrix 130. The support member 115 retains the matrix 130 against the tooth abutting face 112. A top ledge 115 enables pressure to be applied to the matrix 130 as the matrix is inserted into the inter-proximal space. The top ledge, 115 runs from the support member 115 towards the ridge 113.

The matrix 130 is able to horizontally slide within the slot 114 in the lugs 110. A further support member 118 aids in the retention to the matrix 130 by increasing the resistance to the matrix falling out of the slot To increase the resistance the face of the support member 118 that contacts the matrix 130 is further towards the face of support member 115 that contacts the matrix than the face 112 of the lug 110, requiring the matrix to follow a controlled path between them.

The lugs 110 additionally have a channel 119 that in use runs from the ridge 113. When the lugs 110 are assembled with the spring 101 the slot is substantially perpendicular to the spring arms 102. Referring to FIG. 1 in use the wedge 120 is threaded through channels 119 of each lug to span across the gap between the lugs. Outward portions of the wedge 120 pass through channels 105 of the spring arm 102 and are cleated thereby. The channel 119 of each lug is contoured in a "V" shape to enable the wedge to be inserted or threaded into the channel.

The lugs 110 are made of acetyl but could be made of any suitable plastic or metal in particular stainless steel. In the preferred embodiment the lugs 110 are transparent to enable light used to cure acrylic filling. A light shined from above the lugs will be reflected towards the filling to be cured as shown by arrow 150 in FIG. 14.

Figure 22:
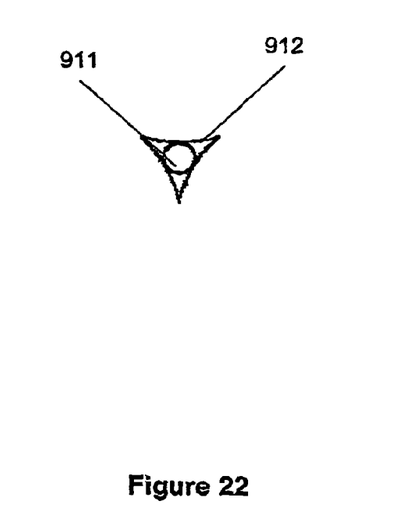
FIG. 22 is an end view of the wedge of the present invention.
Figure 23:
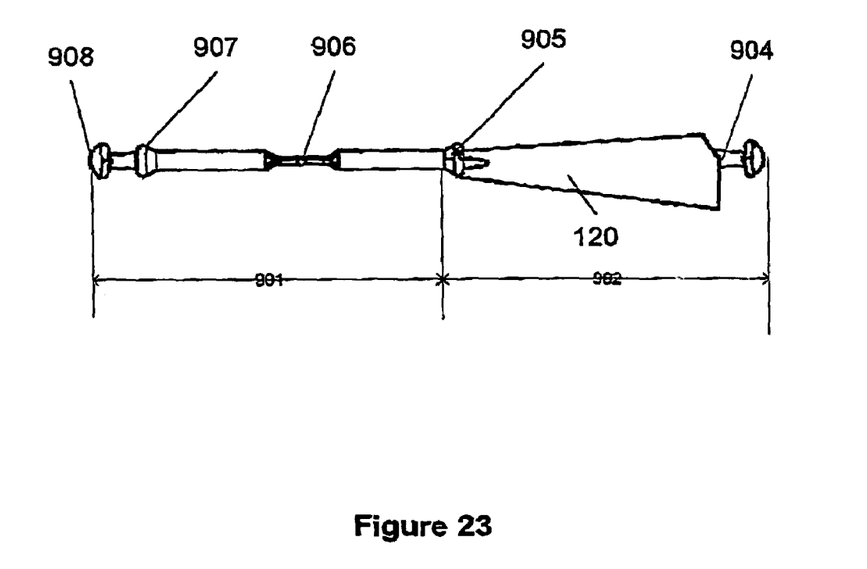
FIG. 23 is a side view of the wedge of the present invention.
Figure 24:
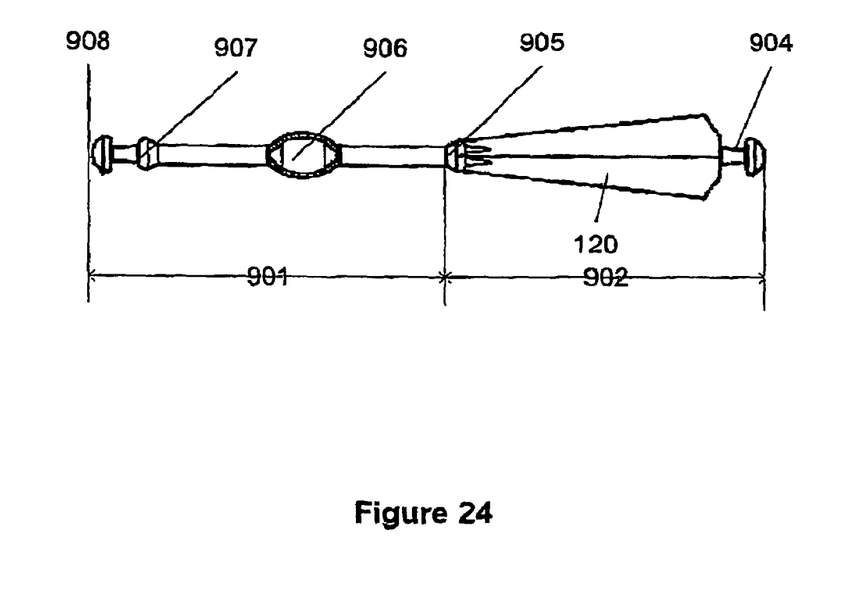
FIG. 24 is an alternative side view of the wedge of the present invention.

Referring to FIGS. 21 to 24 the wedge 120 comprises a one piece member of elastic material such as rubber, polyurethane or other suitable material. In the preferred embodiment polyurethane is used as it has suitable elasticity properties but any other material that has like elasticity properties would be suitable. Suitable elasticity properties require the wedge to stretch approximately 40%. The elastic wedge 120 has an elongate narrow section marked 901 and elongate tapered section marked 902. The narrow section 901 is a cylindrical section as seen in FIG. 22. The narrow section 901 has a diameter of 0.5 to 1.5 and a length of 10 to 15 millimeters. In an alternative embodiment an oval or other cross sectional shape could be used, but it is preferred that the shape is in general "round". For example in the preferred circular form it has an aspect ratio of 1, and the minimum perimeter squared to area ratio of 4π.

The elongated tapered section 902 has a maximum thickness of 3 to 5 millimeters and an approximate length of 10 to 15 millimeters. In the preferred embodiment the cross section shown in FIG. 22 is an equilateral triangle but any triangular or other shape would be also be suitable. In the preferred embodiment the faces of the tapered section are concave.

At the end of the elongated taper section 902 at the point where it joins the elongated narrow section 901 there is an integrated bead 905 which is wider than the elongated narrow section 901. At the free end of the elongated tapered section 902 there is a small elongated narrow section 904 and intrinsic bead 903. The integrated bead 903 is wider in cross section than the narrow section 904.

The elongated narrow section 901 has at the free end a bead 908 which is wider in cross section than the elongated narrow section. A short distance from the free end of the elongated narrow section 901 and from bead 908 there is an additional bead 907 which is wider in cross section than the elongate narrow section. In the preferred embodiment this bead is 3 to 5 millimeters from the bead 908 at the end of the narrow section 901.

In approximately the middle of the elongate narrow section 901 there is a flattened section 906. In its narrowest orientation flat section 906 shown in FIG. 23 has a thickness smaller than the thickness of the elongate narrow section 901. In the broadest orientation of the flat section 906 shown in FIG. 24 the flat section 906 is wider than the thickness of the elongated narrow section 901. In the preferred embodiment the flat section 906 of the elongated narrow section 901 is 3 to 8 millimeters long. The flat section 906 makes it easier for the dental professional to use the wedge of the present invention as it passes more easily between two teeth.

The wedge 120 is attached to the lugs 110 and the spring 101 in the following manner. The narrow section 901 is fed through the cleat 105 in a first lug 110 with bead 907 above the cleat 105. The wedge is passed across the channels 119 in the lugs 110 with the flat section 906 spanning the gap between the lugs. The flat section 906 of the wedge will only fit into the channel 119 slot one way so that the flat section 906 is parallel to the matrix 130. This can be seen in FIG. 4. The remaining portion of the narrow section 901 is laid across the channel 119 of the other lug 110 and forced into the cleat 105 with the bead 905 above the cleat 105. This leaves the tapered section 902 of the wedge 120 free. The use of bulbous members or beads on the ends of the wedge makes it easier for the dental professional to grip the ends of the wedge either with fingers or with tweezers for later release.

Referring to FIGS. 17 to 20 the matrix 130 of the present invention is formed of materials such as acrylic, thermoplastic or stainless steel. Matrix 130 is formed such that an edge is shaped to conform to the contours of the inter-proximal gingival margin and in particular edge 136 which contacts the gum is curved outwardly from the centre of the matrix to enable the matrix to be used to file deep cavities. The thickness 135 of the matrix 130 is selected so that it is suitable for insertion inter-proximal between teeth. The thickness should be selected so that it provides sufficient rigidly to permit insertion without damage to the matrix 130. In the preferred embodiment the matrix of the present invention is between 0.2 and 0.7 millimeters. In the preferred embodiment the matrix 130 of the present invention has wings 132 that slide into the slots 114 of the lugs 110 so that the matrix 130 is held in place on the retainer.

In the preferred embodiment the matrix 130 is made of stainless steel but brass or another suitable metal could be used. In an alternative embodiment a clear matrix or matrix that transmits light could be used. Clear matrices have the advantage that the transmit light to assist in the curing of filling. A clear matrix could be made of polyester or other suitable plastic.

Figure 2:
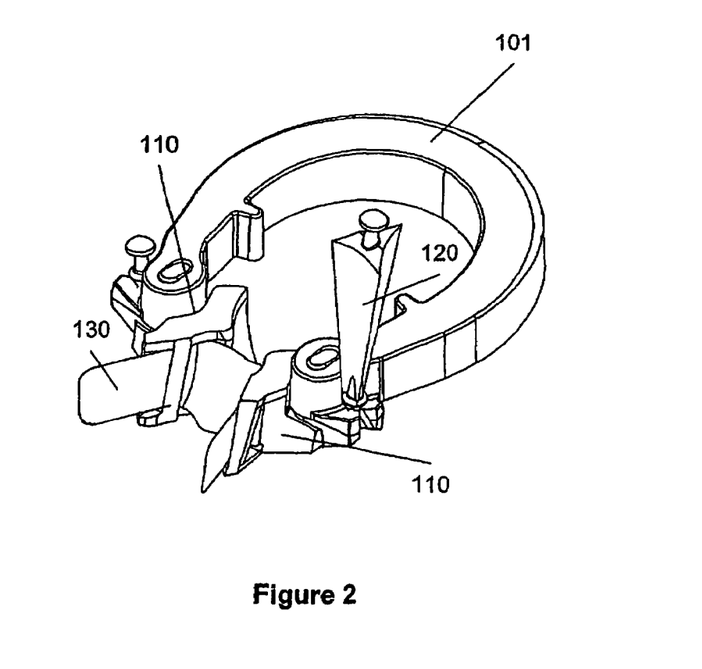
FIG. 2 is a three-dimensional view of the dental matrix system according to the present invention showing the lugs mounted an alternative way.
Figure 3:
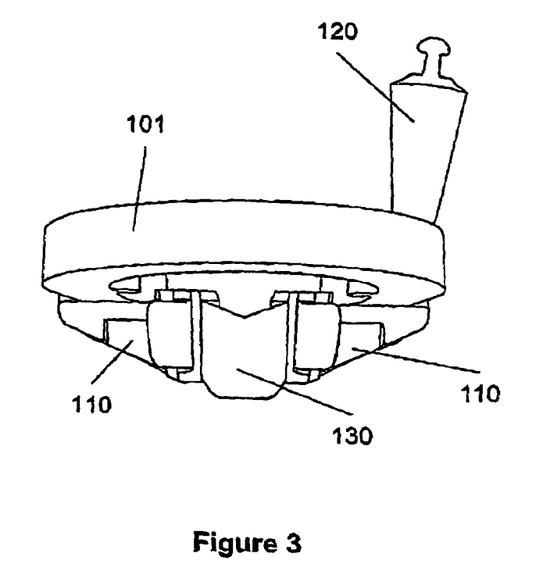
FIG. 3 is an end view of the dental contact matrix system of the present invention.

The dental contact matrix system of the present invention can be assembled either with the matrix facing into the centre of the U-shape seen generally in FIG. 1 or with the matrix facing away from the U-shape seen generally in FIG. 2. The ability to face the matrix either ways makes it easier for the dental professional to use the system as the appropriate assembly for the tooth to be filled can be selected. While the present invention has been described with the spring 101 and lugs 110 as separate components it would be possible to manufacture the components a one piece.

To use the assembled contact matrix system of the present invention the dental professional expands the spring arms 102. This also stretches the narrow section of the wedge 120. In particular the narrow flat section 906 of the wedge 120 is stretched The retainer is then manipulated to place the narrow section of the wedge 901 and the matrix 130 into the inter-proximal space between two teeth. When the dental professional removes the rubber dam forceps the spring 101 contracts and the lugs 110 provide pressure to hold the matrix 130 against the lingual and buccal sides of the tooth to be filled.

Figure 25:
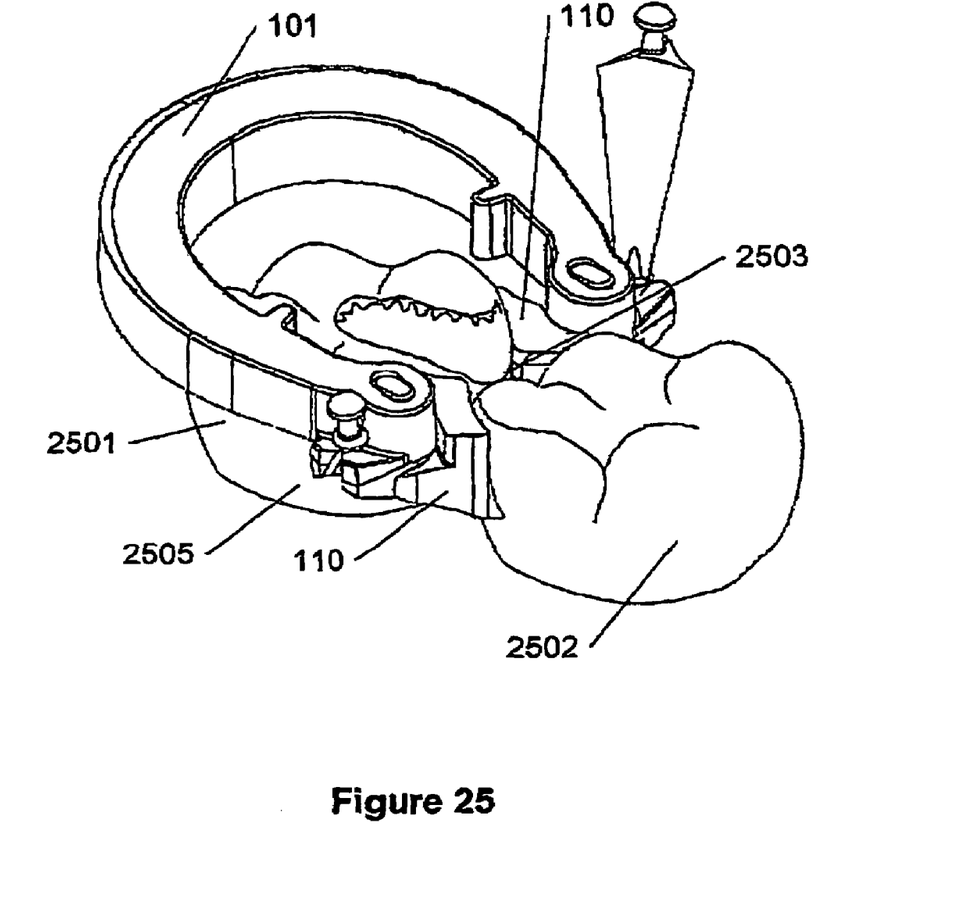
FIG. 25 shows the contact matrix dental system of the present invention in place.

The dental contact matrix system of the preferred embodiment of the present invention is shown in FIG. 25 in place. The tooth to be filled 2501 and the adjacent tooth 2502 are shown. The matrix 130 and narrow portion of the wedge 120 are between the teeth in the inter-proximal space 2503. The lugs 110 are pressing the matrix 130 (not visible) against the tooth surface 2505 thereby holding the matrix 130 in place.

Once in place the dental professional can use tweezers or another suitable tools to detach the ends of the elastic wedge from the cleats 105 of the spring 101. Beads 908 and 903 make this process easier by preventing the tweezers from slipping off the wedge 120

Then using tweezers or other suitable tool, the dental professional pulls on the elongated narrow section 902 and in particular bead 908. This pulls the tapered section 902 into the inter-proximal space between the two teeth to better secure the matrix 130 against the tooth to be filled. The elastic wedge causes continuous lateral pressure.

In the preferred embodiment the lugs, wedge and matrix all transmit light enabling light used to cure the filling to reach the filling material. This has the advantage of enabling the filling to cure faster and to ensure a more complete cure.

While use of the wedge 120 has been described with reference to the dental contact matrix system of the present invention the wedge 120 of the present invention can be used separately to hold various types of matrix bands in place. To use the wedge 120 of the present invention the dental professional would position their preferred matrix band or sectional matrix on the tooth to be filled in the usual manner using fingers and/or tweezers.

The dental professional would then elongate the narrow elongated section 901 of the wedge 120 by stretching it and placing the wedge between the matrix band and the adjacent tooth. The wedge is placed in a similar fashion to the use of dental floss. The dental professional then releases both ends and pulls on the narrow elongated section 901 to pull the elongated tapered section 902 through the gap so that the tapered section passes inter-proximally until the space is tight.

The present invention has the advantage that when the tension on the wedge 120 is released the elastic wedge 120 expands further increasing the pressure on the matrix band and on the adjacent teeth, thereby causing them to separate. The elastic wedge of the present invention, because it does not have a point and is pulled or threaded into the inter-proximal space, is gentler on the gingival tissue and thereby less traumatic for dental patients.

The present dental contact matrix system of the invention can be assembled before being placed in the patients mouth saving the dental professional time and reducing the chance of dropping a matrix or wedges into a patients mouth.

The invention claimed is:

1. A retainer for placing and retaining a matrix in a dental contact matrix system, and for use in conjunction with an elastic "wedge", said retainer comprising:
   a first lug, to fit on one side of a proximal contact between two teeth,
   a second lug to fit on the other side of said proximal contact,
   a spring member connecting between said first lug and said second lug, said spring member holding said lugs such that they must be separated to fit over said proximal contact, wherein the spring member applies a restorative force pressing said lugs against opposed sides of said proximal contact, and
   means for receiving and holding an elastic wedge in a stretched condition to span between said first lug and said second lug.

2. The retainer as claimed in claim 1 for use in conjunction with a wedge comprising a one piece member of elastic material and having:
   an elongate narrow section, and
   an elongate tapered section with a triangular cross section, said elongate narrow section extending from the narrow end of said tapered section;
   wherein each said lug of said retainer includes a ridge for projecting into the proximal contact, and said means for receiving and holding an elastic wedge receives and holds said wedge with said elongate narrow section spanning between said ridge of said first lug and said ridge of said second lug.

3. The retainer as claimed in claim 2 wherein said means for receiving and holding an elastic wedge comprises:
   a first wedge engagement associated with said first lug,
   a guide on said first lug to have said wedge exit from underneath said first lug at said ridge,
   a second wedge engagement associated with said second lug,
   a guide on said second lug to have said wedge exit from underneath said second lug at said ridge.

4. The retainer as claimed in claim 3 wherein said first and second wedge engagements each comprise a cleat formed in an end of said spring member adjacent the connection between said spring member and the respective said lug.

5. A dental contact matrix system including a retainer for placing and retaining a matrix in a dental contact matrix system, an elastic "wedge" and a matrix, said retainer comprising:
   a first lug, to fit on one side of a proximal contact between two teeth,
   a second lug to fit on the other side of said proximal contact, and
   a spring member connecting between said first lug and said second lug, said spring member holding said lugs such that they must be separated to fit over said proximal contact, wherein the spring member applies a restorative force pressing said lugs against opposed sides of said proximal contact;
   said elastic wedge being held in a stretched condition spanning between said first lug and said second lug.

6. The dental contact matrix system as claimed in claim 5 wherein said wedge has:
   an elongate narrow section, and
   an elongate tapered section with a triangular cross section, said elongate narrow section extending from the narrow end of said tapered section;
   each said lug includes a ridge for projecting into the proximal contact,
   and said means for receiving and holding an elastic wedge holds said wedge with said elongate narrow section spanning between said ridge of said first lug and said ridge of said second lug.

7. The dental contact matrix system as claimed in claim 6 wherein said means for receiving and holding an elastic wedge comprises:
   a first wedge engagement associated with said first lug,
   a guide on said first lug to have said wedge exit from underneath said first lug at said ridge,
   a second wedge engagement associated with said second lug,
   a guide on said second lug to have said wedge exit from underneath said second lug at said ridge.

8. The dental contact matrix system as claimed in claim 7 wherein said first and second wedge engagements each comprise a cleat formed in an end of said spring member adjacent the connection between said spring member and the respective said lug, said narrow section of said wedge engaging in each said cleat.

9. A retainer for placing and retaining a matrix in a dental contact matrix system, and for use in conjunction with an elastic "wedge", said retainer comprising:
   a first lug, to fit on one side of a proximal contact between two teeth,
   a second lug to fit on the other side of said proximal contact,
   a first matrix support member positioned to retain a matrix against said first lug,
   a second matrix support member positioned to retain a matrix against said second lug, and
   a spring member connecting between said first lug and said second lug, said spring member holding said lugs such that they must be separated to fit over said proximal contact, wherein the spring member applies a restorative force pressing said lugs against opposed sides of said proximal contact.

10. The retainer as claimed in claim 9 wherein:
    said first lug includes a pair of tooth abutting faces, said tooth abutting faces meeting at a ridge for projecting into the proximal contact between two teeth,
    said first matrix support member is positioned to retain a matrix against one said tooth abutting face, being a support face,
    said second lug includes a pair of tooth abutting faces opposing said tooth abutting faces of said first lug, said tooth abutting faces meeting at a ridge for projecting into proximal contact between two teeth, said ridge opposing said ridge of said first lug, and
    said second matrix support member is positioned to retain a matrix against the said tooth abutting face of said second lug that is opposed to said support face of said first lug, being a support face of said second lug.

11. The retainer as claimed in claim 10 wherein each said lug includes a ledge extending forward from said support face along an upper edge of said support face, to in use bear against the upper edge of a dental contact matrix held against said support face by a respective support member.

12. The retainer as claimed in claim 10 wherein said spring member follows an open loop path largely in a plane substantially perpendicular to the direction of said ridges of said lugs and above said lugs, to leave the space between said lugs unobscured by said spring member when viewed from above said plane.

13. The retainer as claimed in claim 12 including a releasable engagement between each said first and second lug and said spring member, each said releasable engagement allowing for connection of each of said first lug and said second lug, such that said first and second lugs may be mounted to said spring member in:
- a first condition wherein said support faces of said first lug and said second lug face away from said open loop path of said spring member, and
- a second condition wherein said support faces of said first lug and said second lug face toward said open loop path of said spring member.

14. The retainer as claimed in claim 13 wherein said releasable engagement comprises a plug and socket, engageable along an engagement axis, said engagement axis being parallel with said ridges of said first and second lugs, and being near perpendicular to said plane of said open loop path.

15. The retainer as claimed in claim 12, for use in conjunction with a wedge comprising a one piece member of elastic material, and having:
- an elongate narrow section, and
- an elongate tapered section with a triangular cross section, said elongate narrow section extending from the narrow end of said tapered section,
- wherein said retaining member includes means for receiving and holding said wedge with said elongate narrow section spanning between said ridge of said first lug and said ridge of said second lug.

16. The retainer as claimed in claim 15 wherein said means for receiving and holding an elastic wedge comprises:
- a first wedge engagement associated with said first lug,
- a guide on said first lug to have said wedge exit from underneath said first lug at said ridge,
- a second wedge engagement associated with said second lug, and
- a guide on said second lug to have said wedge exit from underneath said second lug at said ridge.

17. The retainer as claimed in claim 16 wherein said first and second wedge engagements each comprise a cleat formed in an end of said spring member adjacent the connection between said spring member and the respective said lug.

18. The retainer as claimed in claim 12 including an arrangement for enabling an expansion tool to expand said spring member, said arrangement including a pair of engagements on said spring member, each engagement near a respective said lug.

19. The retainer as claimed in claim 18 wherein each said engagement comprises an inward protrusion from said spring member.

20. The retainer as claimed in claim 9 wherein said first matrix support member is connected with said first lug, and is spaced from a support face of said first lug.

21. The retainer as claimed in claim 20 wherein said first matrix support member is substantially parallel with said support face, and is spaced forward of said support face, and outward of an edge of said support face away from said ridge.

22. The retainer as claimed in claim 21 including a further support member connected with said first lug, parallel with said first support member, and spaced further out and behind said first support member.

23. The retainer as claimed in claim 20 wherein said second matrix support member is connected with said second lug, and is spaced from said support face of said second lug.

24. The retainer as claimed in claim 23 wherein said second matrix support member is substantially parallel with said support face, and is spaced forward of said support face, and outward of an edge of support face away from said ridge.

25. The retainer as claimed in claim 24 including a further support member connected with said second lug, parallel with said second support member, and spaced further out and behind said second support member.

26. The retainer as claimed in claim 9 wherein at least one said lug is formed from a light transmissive material.

27. The retainer as claimed in claim 26 wherein said light transmissive lug is formed such that at least a good proportion of light entering said lug from above exits said lug toward said teeth.

* * * * *